United States Patent [19]
Seitz

[11] Patent Number: 5,361,778
[45] Date of Patent: Nov. 8, 1994

[54] METHOD AND APPARATUS FOR SENSING AND EVALUATING FOOT BORNE MOTION

[76] Inventor: Ronald H. Seitz, 3202 E. Race St., Visalia, Calif. 93291

[21] Appl. No.: 9,237

[22] Filed: Jan. 26, 1993

[51] Int. Cl.⁵ .............................................. A61B 5/00
[52] U.S. Cl. .................................................. 128/779
[58] Field of Search ................... 128/774, 779; 73/172; 340/573

[56] References Cited

U.S. PATENT DOCUMENTS

| | | |
|---|---|---|
| 2,253,996 | 8/1941 | Bechman . |
| 3,352,559 | 11/1967 | Larsen . |
| 3,791,375 | 2/1974 | Pfeiffer ................................ 128/779 |
| 3,974,491 | 8/1976 | Sipe .................................... 128/779 |
| 4,099,713 | 7/1978 | Spector . |
| 4,320,895 | 3/1982 | Muller . |
| 4,463,946 | 8/1984 | Wallace et al. . |
| 4,647,918 | 3/1987 | Goforth ............................... 128/779 |
| 4,745,930 | 5/1988 | Confer ................................. 128/779 |
| 4,759,542 | 7/1988 | Hudec . |
| 4,944,309 | 7/1990 | Mechling . |

FOREIGN PATENT DOCUMENTS 2641183  7/1990  France ................................ 128/779

Primary Examiner—Max Hindenburg
Attorney, Agent, or Firm—Worrel & Worrel

[57] ABSTRACT

A method for evaluating foot borne motion in an individual including causing the individual to engage in the foot borne motion; and detecting predetermined movement relative to a foot of the individual during the foot borne motion. An apparatus for evaluating foot borne motion in an individual including a support member, footwear for attaching the support member to a foot of the individual, and a sensor borne by the apparatus for detecting predetermined movement of the foot during the foot borne motion.

19 Claims, 3 Drawing Sheets

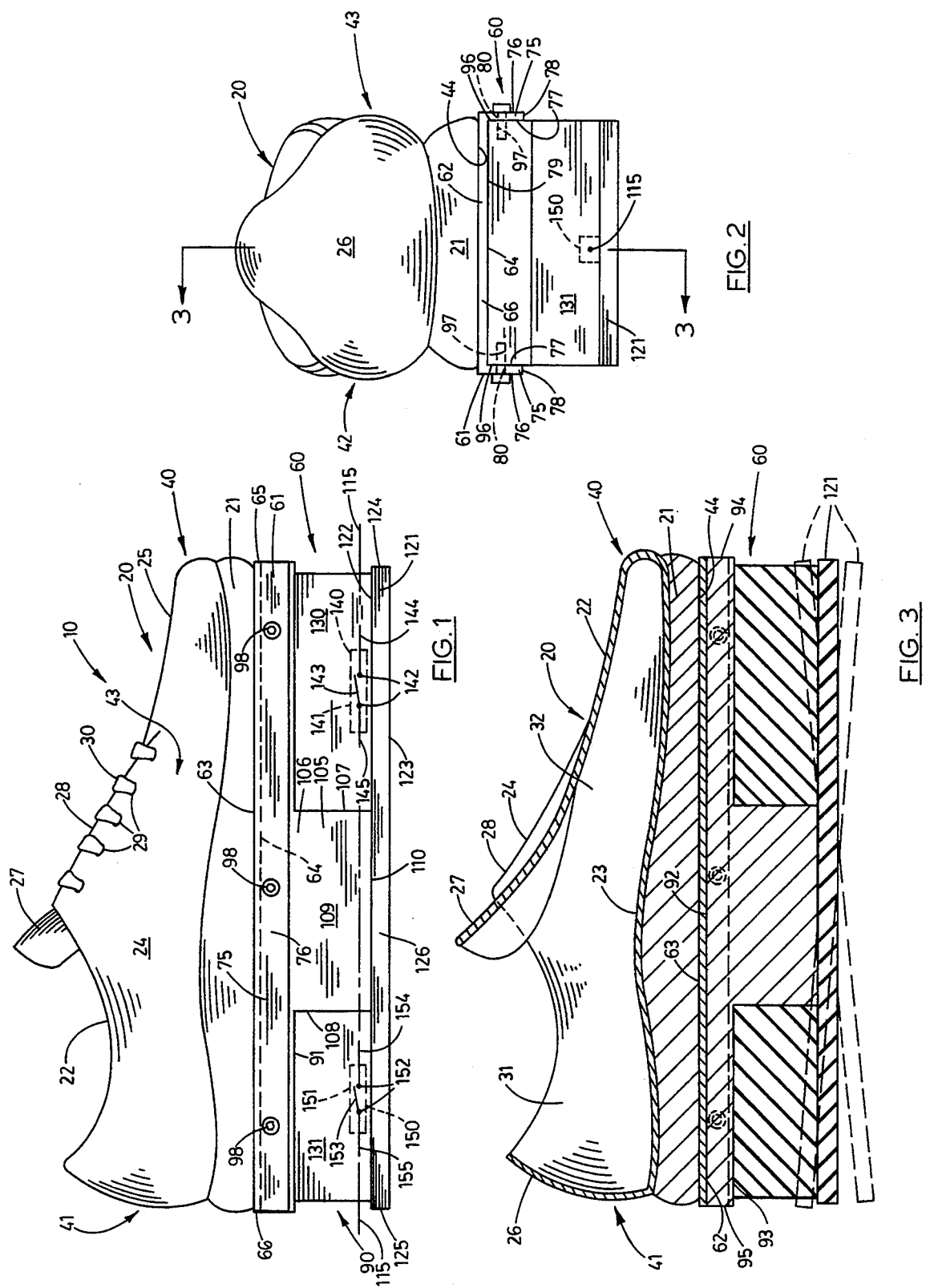

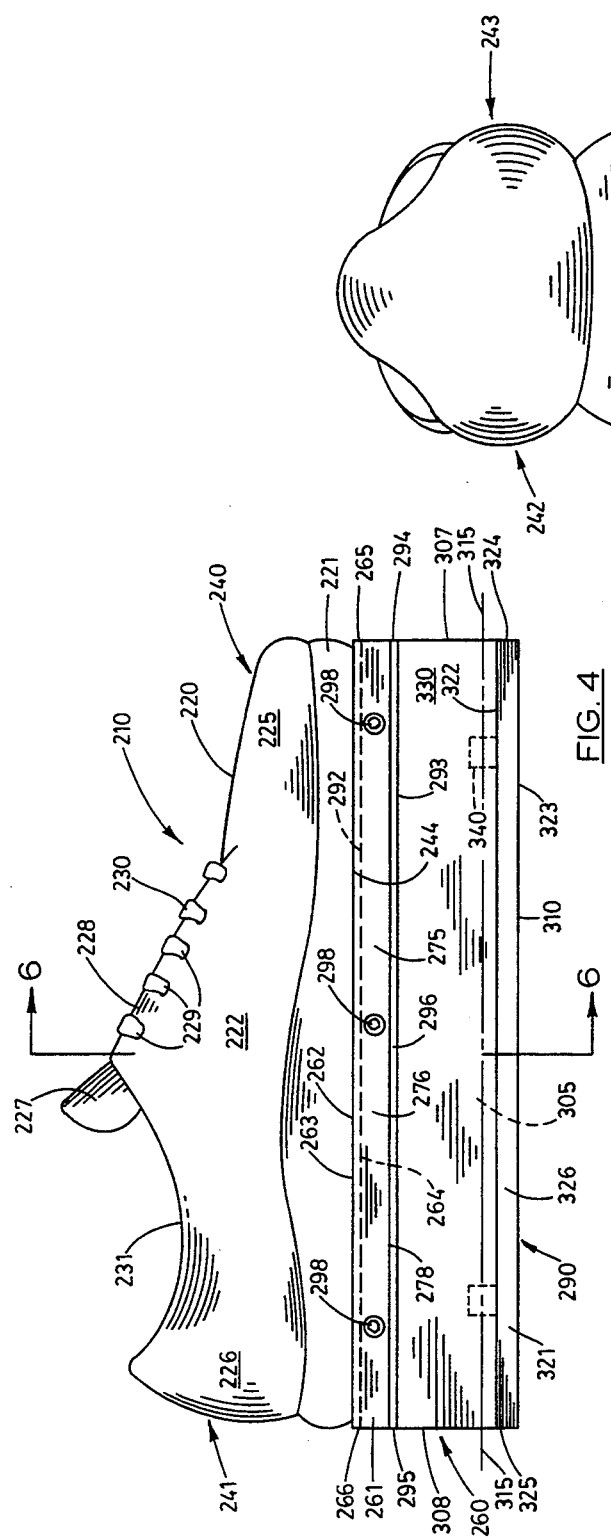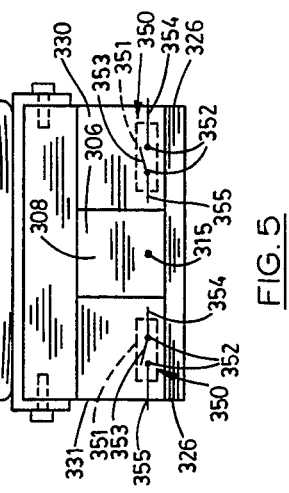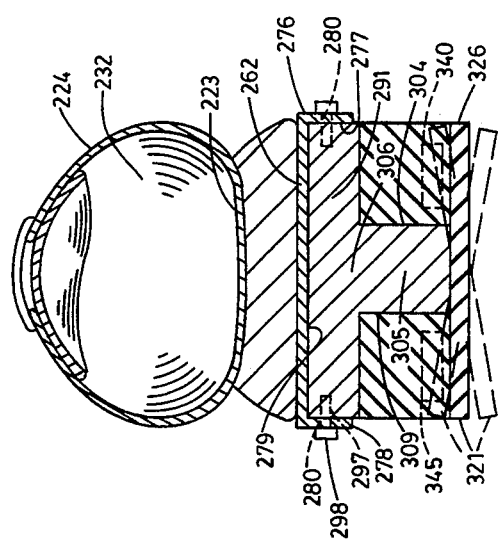

METHOD AND APPARATUS FOR SENSING AND EVALUATING FOOT BORNE MOTION

BACKGROUND OF THE INVENTION

1. Field of the Invention

The present invention relates to a method and apparatus for sensing and evaluating foot borne motion and, more particularly, to such a method and apparatus which are particularly well suited to detecting predetermined movement in such foot borne motion for the purpose of evaluating the physical capabilities of the individual so as to assist in the rehabilitation of individuals suffering from diminished capability as a result, for example, of injury, age, disease, or the like.

2. Description of the Prior Art

Science and medicine have long devoted considerable attention to the rehabilitation of individuals suffering from diminished capability in physical activity as the result of any one or more of a host of different causes. These causes may include birth defects, physical injury, disease, aging and the like. To a large degree, such rehabilitation has been devoted primarily to strengthening muscles of the human body and practicing a sense of balance so as to develop the physical skills required to carry on the physical activity, or more effectively to do so. Only relatively recently has it become known that a complex interplay of physical and mental attributes are required for successfully performing the particular physical activity to which attention is devoted. These physical and mental attributes are affected by the particular injuries, or disabilities, which are the cause of the lack of success in performing the physical activity under scrutiny.

One physical activity which is of considerable importance in daily life is perambulation, or walking. The ability to walk is of central importance in most daily activities. Accordingly, considerable attention has been devoted by science and medicine to the rehabilitation of individuals suffering from diminished capacity in this regard. However, the ability to walk is dependent upon a host of factors which are still being discovered and evaluated. In this regard, it has long been known that a sense of balance is critical to this physical activity. However, it has only recently become known that balance itself is dependent upon a combination of complex factors.

Balance is generally viewed as dependent upon the ability to maintain the body's center of gravity over its base of support. In walking, of course, the base of support of the body is moving and otherwise shifting, so that constant adjustment of the center of gravity is required. Perception of the center of gravity is dependent upon sensing by the vestibular system of the inner ear, the somatosensory system and by vision. The particular combination of these three senses employed during walking and other physical activity is dependent upon the context of the situation to which the individual is subjected.

Once the center of gravity has moved beyond the base of support of the human body, the limit of stability is exceeded and the individual will either fall or take a step. During walking, of course, the individual takes a continuous series of steps during which such balance must be maintained using the senses to which reference has previously been made. However, other physical attributes may be employed in maintaining such balance during walking which must be taken into consideration when designing a program for the physical rehabilitation of the individual. Thus, the strength of the individual, as may be affected by the root cause of the disability, such as birth defect, injury, aging, disease and the like, determines the body's ability to maintain balance once imbalance is sensed. Similarly, the period of time required by an individual to sense imbalance so as to leave time to adjust to such imbalance is another factor having a bearing in the matter. Still further, the individual's ability at points of the body adequately to perform flexion and extension has a bearing on the individual's ability to maintain balance. Thus, the individual's ability to achieve flexion and extension in the ankle and hip also have a bearing on the individual's ability to maintain balance during walking and therefore the ability adequately to perform this physical activity.

While there are a variety of other considerations which influence the individual's ability to perform such physical activities as walking, there has not heretofore been an adequate method or device capable of sensing and evaluating the individual's physical capabilities in these regards in a manner conducive to the development of a rehabilitation program operable most effectively to achieve the rehabilitation desired.

Therefore, it has long been known that it would be desirable to have a method and apparatus for sensing and evaluating foot borne motion which are operable effectively to isolate and measure the physical capabilities required for such foot borne motion; which have a wide application to individuals having a multitude of different physical capabilities; which are similarly adapted to sensing and evaluating a variety of foot borne motions including walking and running; and which can conveniently and inexpensively be employed by doctors, physical therapists and others in the testing and/or treatment of individuals requiring such rehabilitation.

SUMMARY OF THE INVENTION

Therefore, it is an object of the present invention to provide an improved method and apparatus for sensing and evaluating foot borne motion.

Another object is to provide such a method and apparatus which are particularly well suited to the sensing and evaluating of the physical capability of an individual in walking so as to permit the selection of a program of physical therapy most suited to the physical disabilities of the individual.

Another object is to provide such a method and apparatus which can be employed to apply an infinitely varied combination of physical conditions to the individual during such foot borne motion so as fully to test the physical capabilities of the individual under nearly all circumstances.

Another object is to provide such a method and apparatus which themselves can be employed as tools in the rehabilitation of the individual.

Another object is to provide such a method and apparatus which are adaptable to a virtually unlimited number of physical disabilities and are adaptable by the person testing the individual to seek the information desired in achieving the rehabilitation required.

Further objects and advantages are to provide improved elements and arrangements thereof in an apparatus for the purpose described which is dependable, economical, durable and fully effective in accomplishing its intended purpose.

These and other objects and advantages are achieved, in the preferred embodiments of the method and apparatus of the present invention, in a method for evaluating foot borne motion in an individual including: applying footwear to a foot of the individual having a sensor operable to detect predetermined movement during the foot borne motion; causing the individual to engage in the foot borne motion; and registering the predetermined movement detected by the sensor during the foot borne motion.

BRIEF DESCRIPTION OF THE DRAWINGS

FIG. 1 is a side elevation of the first embodiment of the apparatus of the present invention employed in the practice of the method of the present invention.

FIG. 2 is a rear elevation of the apparatus of FIG. 1.

FIG. 3 is a longitudinal vertical section taken on line 3—3 in FIG. 2.

FIG. 4 is a side elevation of the apparatus of the second embodiment of the present invention employed in the practice of the method of the present invention.

FIG. 5 is a rear elevation of the apparatus of FIG. 4.

FIG. 6 is a transverse vertical section taken on line 6—6 in FIG. 4.

DESCRIPTION OF THE PREFERRED EMBODIMENTS

First Embodiment

Figure 8:
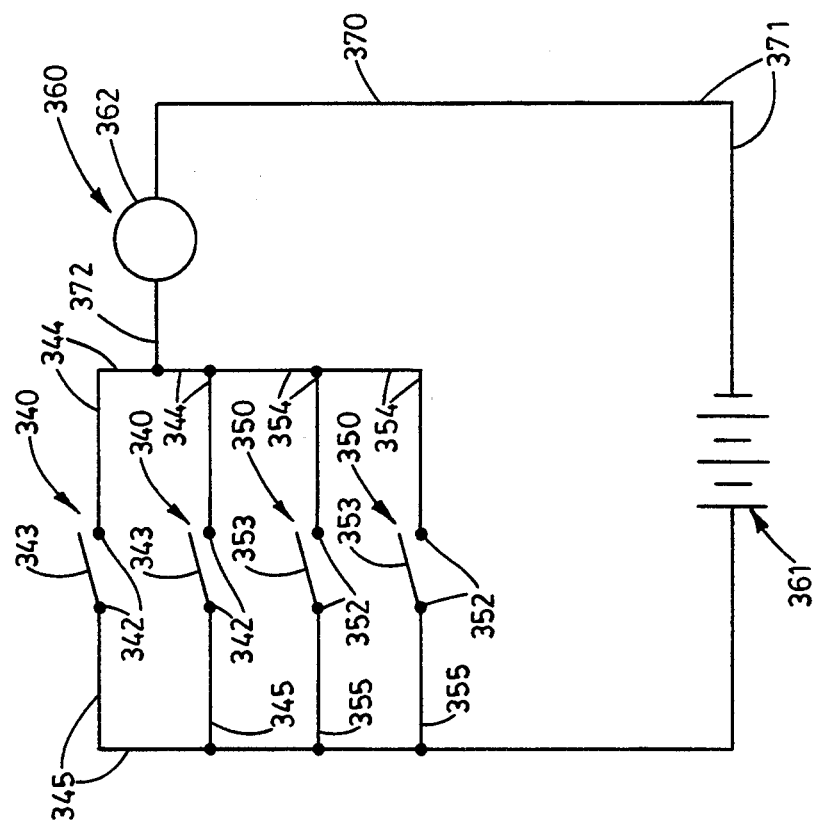
FIG. 8 is a schematic diagram of the electrical sensing system of the second embodiment of the apparatus of the present invention shown in FIGS. 4, 5 and 6.

Referring more particularly to the drawings and principally to FIGS. 1, 2, 3 and 7, the evaluating apparatus of the first embodiment of the invention, employed in the practice of the method hereof, is generally indicated by the numeral 10 in FIG. 1. The apparatus includes footwear or a shoe 20 hereinafter described in greater detail. It will be understood that although the apparatus can be employed, as will hereinafter be described in greater detail, wherein the individual wears only one of the apparatuses on a selected foot, it is contemplated that in most instances, the individual will wear a pair of the apparatuses. For illustrative convenience, only one apparatus is herein described for the first embodiment 10 of the apparatus. In all pertinent respects, both apparatuses worn by an individual are identical with the exception that one shoe is fitted for the left foot and the other is fitted for the right foot. For purposes of illustrative convenience, it will also be visualized that the shoe 20 of the apparatus shown in FIGS. 1, 2 and 3 is the left shoe of the pair.

The shoe 20 has a sole 21 on which is mounted an envelope 22 adapted to receive the foot of the individual wearing the shoe. The envelope has a lower liner 23 and an tipper 24. The envelope has a front portion 25 and a rear, or heal, portion 26. The envelope has a tongue 27 overlapped by front flaps 28. The front flaps have eyelets 29 through which a shoe lace 30 is extended in the conventional manner and employed to secure the shoe on the foot of the individual. The shoe has an ankle opening 31 and an interior 32.

For purposes of describing the operation of the apparatus 10 in the practice of the method of the present invention, it will be understood that the shoe 20 has a front portion 40 and a rear portion 41. The shoe has an outer lateral portion 42 and an opposite inner lateral portion 43. The sole 21 of the shoe has a flat bottom surface 44.

A base assembly 60 is mounted on the sole 21 of the shoe 20. The base assembly includes a mounting frame 61 which has a substantially flat rectangular metal plate 62. The plate has a flat upper surface 63 which is secured, such as by suitable adhesive, on the flat bottom surface 44 of the sole 21. The plate has a flat lower surface 64, a front edge 65 and an opposite rear edge 66.

A pair of parallel side flanges 75 extend downwardly from the lateral edges of the plate 62. Each flange has an exterior surface 76 and an opposite interior surface 77. Each flange has a lower edge 78. The flanges define a channel 79. Three bolt holes 80 extend through each of the side flanges in spaced relation to each other.

The base assembly 60 includes a measuring assembly 90 mounted on the mounting frame 61, as hereinafter described. The measuring assembly 90 can be constructed in a wide variety of embodiments dependent upon the results to be achieved in the practice of the method of the present invention. The embodiment of the measuring assembly described herein is one such embodiment. The measuring assembly includes a substantially flat, rectangular mounting plate 91 which can be constructed of any suitable hard material, such as metal or wood, and which is dimensioned to be received in the channel 79 of the mounting frame 61. The mounting plate has a flat tipper surface 92 and an opposite flat lower surface 93. The mounting plate has a front surface 94 and an opposite parallel rear surface 95. The mounting plate has parallel side surfaces 96 into which internally screw threaded bolt holes 97 are extended in a pattern corresponding to the bolt holes 80 of the side flanges 75. Bolts 98 are individually extended through the bolt holes 80 of the side flanges and are screw-threadably received in the screw threaded bolt holes 97 to mount the mounting plate 91 within the channel 79 of the mounting frame 61.

A support block 105 is mounted on and extended downwardly from the lower surface 93 of the mounting plate 91 substantially centrally thereof. The support block is preferably integral with the mounting plate 91 and is thus constructed of the same material as the mounting plate. Alternatively, the support block can be constructed of a material of greater flexibility such as crepe rubber, or synthetic rubber. The optimum shape and position of the support block of the measuring assembly is dependent upon the objectives to be achieved in the practice of the method of the present invention. Accordingly, the specific structure herein described is only representative of one such embodiment. The support block has an tipper portion 106, a flat front surface 107, a flat substantially parallel rear surface 108 and parallel side surfaces 109. The support block has a lower surface 110. For purposes of illustrative convenience, it will be understood that a longitudinal axis for the measuring assembly extends through the support block as shown in FIGS. 1 and 2.

A base plate 121 is mounted on the lower surface 110 of the support block 105. The base plate is preferably constructed of crepe rubber, or synthetic rubber, so as to be of moderate flexibility. The base plate is adhesively mounted on the lower surface 110 of the support block. The base plate has a flat upper surface 122, a flat lower surface 123, a front surface 124 and a parallel rear surface 125. The base plate has parallel side surfaces 126. The area defined by the front surface 107 of the support block, the lower surface 93 of the mounting plate 91 and the tipper surface 122 of the base plate 121 is filled with front filling material 130, preferably a block of crepe rubber, or synthetic rubber, adhesively mounted in position. Similarly, the area defined by the rear surface 108 of the support block, the lower surface 93 of the mounting plate and the upper surface 122 of the base plate is filled with rear filling material 131 such as crepe rubber, or synthetic rubber, adhesively mounted in position. Thus, it will be seen that since the base plate 121, and front and rear filling material is of moderate flexibility, the base plate in use is of moderate flexibility such as may be visualized upon reference to FIG. 3. In FIG. 3, the base plate is shown in full lines in an unflexed position and in phantom lines in flexed positions.

A sensor, or front mercury switch, 140 is mounted by any suitable means within the front filling material 130, as shown in FIG. 1. The mercury switch has a switch housing 141, electrical contacts 142, and a switch closure 143. The front mercury switch has a first electrical conductor 144 connected to one of the electrical contacts 142 and a second electrical conductor 145 operably connected to the other of the electrical contacts 142. The front mercury switch is of a normally open type. Thus, it remains open when the mercury switch is in a horizontal attitude and closes only after the front mercury switch is moved to and beyond a predetermined attitude sufficiently deviated from horizontal.

Similarly, a rear sensor, or rear mercury switch, 150 is mounted by any suitable means within the rear filling material 131, as shown in FIG. 1. The rear mercury switch has a switch housing 151, electrical contacts 152 and a switch closure 153. A first electrical conductor 154 is operably connected to one of the electrical contacts 152. A second electrical conductor 155 is operably connected to the other of the electrical contacts 152. As with the front mercury switch 140, the rear mercury switch is of the normally open type when the switch housing is disposed in a horizontal attitude. The switch closure closes upon the switch housing being moved to and beyond a predetermined attitude deviated from horizontal.

Figure 7:
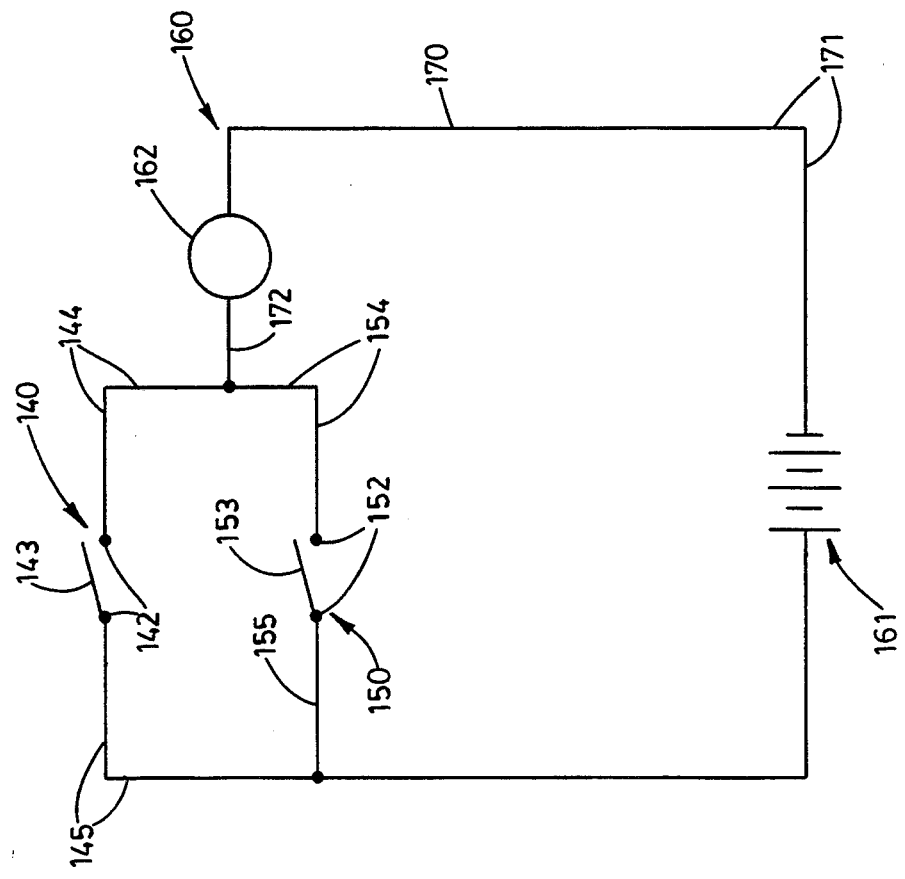
FIG. 7 is a schematic diagram of the electrical sensing system of the apparatus of the first embodiment of the apparatus shown in FIGS. 1, 2 and 3.

An electrical sensing system 160 for the apparatus 10 is shown in FIG. 7. The electrical sensing system includes a source of electrical energy 161 which can be a battery housed, for example, within the measuring assembly, or can be remote, such as a well outlet to which the electrical sensing system is connected through a suitable electrical cable, not shown. The electrical sensing system further includes a sound generating mechanism, or buzzer, 162 and the front and rear mercury switches 140 and 150, respectively. The buzzer can be mounted in any convenient location in the measuring assembly. The electrical sensing system includes an electrical circuit 170 having an electrical conductor 171 interconnecting the source of electrical energy 161 and the buzzer 162. An electrical conductor 172 extends from the buzzer 162 and is connected to the first electrical conductor 144 of the front mercury switch. Second electrical conductor 145 is extended from the front mercury switch and is connected to the source of electrical energy 161. Electrical conductor 172 is also connected to the first electrical conductor 154 of the rear mercury switch 150. The second electrical conductor 155 of the rear mercury switch is connected to the second electrical conductor 145 to complete the circuit. Thus, it will be seen that if either or both of the front and rear mercury switches 140 and 150 are closed, electrical energy is supplied from the source to operate the buzzer 162.

Second Embodiment

The apparatus of the second embodiment of the present invention, employed in the practice in the method hereof, is generally indicated by the numeral 210 and is shown in FIGS. 4, 5, 6 and 8.

For illustrative convenience, it will be understood that, except as otherwise noted, apparatus 210 is identical to apparatus 10. Thus, apparatus 210 has a footwear or shoe 220 which, as with apparatus 10, can be used individually or, as normally envisioned, in a pair worn by an individual. For illustrative convenience, only one such shoe 220 is described herein. The shoes 220 of the pair are identical except as varied as necessary to fit the feet of the individual. For illustrative convenience, it will be understood that the shoe 220 shown in FIGS. 4, 5 and 6 is adapted to be worn by the left foot of the individual.

The shoe has a sole 221 on which is mounted an envelope 222. The envelope has a lower liner 223 on which is mounted an upper 224. The upper has a front portion 225 and an opposite rear, or heal, portion 226. The upper has a tongue 227 overlaid by front flaps 228. The front flaps are individually pierced by eyelets 229 through which a shoe lace 230 is extended in the conventional fashion for purposes of securing the shoe on the foot of the individual. The shoe has an ankle opening 231 and an interior 232.

For purposes of illustrative convenience, it will be understood that the shoe 220 has a front portion 240, a rear portion 241, an outer lateral portion 242, an inner lateral portion 243 and a flat bottom surface 244.

The apparatus 210 has a base assembly 260 mounted on the sole 221 of the shoe 220. The base assembly includes a mounting frame 261 including a flat rectangular plate 262 adhesively mounted on the flat bottom surface 244 of the sole 221. The plate has a flat upper surface 263 which is adhesively mounted on the flat bottom surface 244, a flat lower surface 264, a front edge 265 and a rear edge 266. A pair of side flanges 275 extend downwardly from the lateral edges of the plate 262. Each flange has an exterior surface 276 and an interior surface 277. Each side flange has a lower edge 278 and the side flange is defined a channel 279. Each side flange has three bolt holes 280 extended therethrough.

A measuring assembly 290 is mounted on the mounting frame 261. The measuring assembly includes a mounting plate 291 dimensioned to be received in the channel 279. The mounting plate has a flat tipper surface 292, and a flat lower surface 293. The mounting plate has a front surface 294 and an opposite parallel rear surface 295. The mounting plate has parallel side surfaces 296. The side surfaces have internally screw threaded bolt holes 297 extending therethrough in patterns corresponding to the bolt holes 280 of the side of the side flanges 275. Bolts 298 are individually received in the bolt holes 280 and screw-threadably secured in the bolt holes 297 to mount the mounting plate on the mounting frame 261.

A support block 305 is integral with and extends downwardly from the lower surface 293 of the mounting plate 291. The support block can be constructed of metal, wood, crepe rubber or any other suitable material. The support block 305 is otherwise different from the support block 105 of apparatus 10 of the first embodiment of the present invention. The support block 305 extends the full length of the mounting plate 291 and has an upper portion 306, a front surface 307 coextensive with the front surface 294 of the mounting plate 291 and a rear surface 308 coextensive with the rear surface 295 of the mounting plate. The support block has parallel side surfaces 309 and a substantially flat lower surface 310. For purposes of illustrative convenience, it will be understood that the measuring assembly is oriented along a longitudinal axis 315 shown in FIGS. 4 and 5 and extending through the support block.

A flat base plate 321 is mounted on the lower surface 310 of the support block 305. The base plate is preferably constructed of crepe rubber, or synthetic rubber, so as to possess moderate flexibility. The base plate has a flat upper surface 322 which is adhesively secured on the lower surface 310 of the support block 305. A base plate has a flat lower surface 323, front surface 324, and rear surface 325. The base plate has parallel side surfaces 326.

The area defined by the right side surface 309 of the support block 305, the lower surface 293 of the mounting plate 29 1 and the upper surface 322 of the base plate is filled with interior filling material 330. The area defined by the left side surface 309 of the support block 305, the upper surface 292 of the base plate 291 and the upper surface 322 of the base plate 321 is filled by anterior filling material 331. The filling material 330 and 331 is preferably constructed of crepe rubber, or synthetic rubber, possessing moderate flexibility. The filling material is, in each case, adhesively mounted in position. Thus, it will be seen that the base plate 321 possesses moderate flexibility laterally of the support block 305, but not centrally of the forward portion or rearward portion of the base plate.

A pair of front mercury switches 340 are mounted by any suitable means in the forward portion of the measuring assembly individually within the interior and anterior filling material 330 and 331 on opposite sides of the support block 305. The front mercury switches are oriented along a common axis right angularly related to the longitudinal axis 3 15 of the support block 305. The front mercury switches each have a switch housing 341, electrical contacts 342, a switch closure 343, a first electrical conductor 344 connected to one of the electrical contacts and a second electrical conductor 345 connected to the other of the electrical contacts. As in the case of the apparatus 10, the front mercury switches are normally open switches when disposed in horizontal attitudes. The switches close when the switches are moved to and beyond predetermined angles deviated from horizontal. A pair of rear mercury switches 350 are mounted by any suitable means in the rearward portion of the measuring assembly 290 aligned along a common axis right angularly related to the longitudinal axis of the support block 305. The rear mercury switches are individually housed within the interior and anterior filling material 330 and 331. Each of the rear mercury switches has a switch housing 351, electrical contacts 352, a switch closure 353, a first electrical conductor 354 operably connected to one of the electrical contacts and a second electrical conductor 355 operably connected to the other of the electrical contacts. The rear mercury switches, as in the case of the front mercury switches, are normally open switches when disposed in horizontal attitudes. The switch closures 353 close upon the rear mercury switches being moved to and beyond predetermined attitudes deviated from horizontal.

The apparatus 210 has an electrical sensing system 360 shown in the schematic diagram of FIG. 8 including the front and rear mercury switches 340 and 350, respectively, a source of electrical energy 361 and a sound generating mechanism, or buzzer, 362. As with apparatus 10, the source of electrical energy can be a battery or a remote outlet as described. The buzzer can be mounted on the measuring assembly at any suitable location. The electrical sensing system includes an electrical circuit 370 including an electrical conductor 371 operably interconnecting the source of electrical energy 361 and the buzzer 362. An electrical conductor 372 operably interconnects the buzzer and electrical conductor 344 of one of the front mercury switches 344. The electrical conductor 345 of that mercury switch is operably connected to the source of electrical energy 361 as shown in the schematic diagram of FIG. 8. Electrical conductor 372 is also operably connected to the first electrical conductor 344 of the other front mercury switch 340. The electrical conductor 345 thereof is connected to the other of the electrical conductors 345. As shown in FIG. 8, electrical conductor 354 of one of the rear mercury switches 350 is connected to one of the electrical conductors 344. The second electrical conductor 355 of that rear mercury switch is operably connected to the electrical conductor 345 as shown in FIG. 8. The electrical conductor 354 of the other of the rear mercury switches 350 is operably connected to the first electrical conductor 354. The second electrical conductor 355 of that rear mercury switch is operably connected to electrical conductor 345. Thus, it will be seen that upon one or more of the mercury switches 340 or 350 being moved to the predetermined attitude beyond horizontal to cause closure of the switch closure 343 or 353 thereof, electrical energy is supplied from the source of electrical energy 361 to the buzzer 362 to cause it to be activated.

Operation

The operation of the described embodiments of the present invention in the practice of the method of the present invention is believed to be clearly apparent and is briefly summarized at this point. The operation of the described embodiments of the method can conveniently be described simultaneously as hereinafter set forth.

Apparatus 10 of the present invention is operable to measure longitudinal tilt during the foot borne motion, such as walking, and permits the acceleration and deceleration thereof to be recorded in accordance with the desires of the doctor, physiotherapist or other person conducting the test.

Apparatus 210 is operable to measure lateral tilt during foot borne motion. It will be apparent that both the apparatus 10 and 210 can be employed to measure longitudinal or lateral tilt with the individual in a stationary position. However, the operative advantages in the method and apparatus of the present invention are most associated with their ability to isolate and quantify those factors associated with the physical capability of the individual to walk. Accordingly, the operation of the apparatuses 10 and 210 in the practice of the method of the present invention is described in relation to walking.

The individual to be tested and/or rehabilitated is fitted with the shoes 20 or 220 depending upon the physical capability to be tested or which is subject to rehabilitation. These shoes are placed upon the feet of the individual in the conventional fashion and secured in position using the laces 30 or 230. As previously noted, normally it is envisioned that the individual wears the apparatuses of the invention on both feet, but there may be circumstances under which the individual is desired by the person conducting the test to wear only one of the apparatuses.

It will be seen that when the individual stands upright and perfectly straight wearing the apparatuses 10 and 210, the mercury switches 140 and 150 of apparatus 10 and the mercury switches 340 and 350 of the apparatus 210 remain open. Thus, electrical energy is not supplied to the buzzer 162 or 362 thereby indicating, in effect, that the base plates 121 and 321 are substantially horizontal. Thereafter, under observation of the person conducting the test, the individual is instructed to walk along a flat course of travel at a velocity as instructed by the person conducting the test. The velocity will, of course, depend upon the physical capabilities of the person being tested and the information desired to be gathered by the person conducting the test. Since in both the apparatus 10 and the apparatus 210, the base plates 121 and 321 and the filling material 130, 131 and 330 and 331 are moderately flexible, a substantial amount of support is supplied thereby during normal walking. However, because of the lack of flexibility of the support blocks 105 and 305, tilting, toward the front and toward the back, in the case of apparatus 10, and laterally, in the case of apparatus 210, is permitted. Thus, as the individual walks, walking is relatively comfortable and therefore natural, but sufficient tilt is permitted for purposes of obtaining the desired information.

Where the support blocks 105 and 305 are constructed of crepe rubber, or synthetic rubber, the moderate flexibility of the measuring assembly allows tilt to take place as well. The optimum material from which the support blocks are constructed and, otherwise, the sizes, positions, widths, lengths and other details of construction of the measuring assemblies can best be determined by the person conducting the test in view of the physical capabilities of the individual being tested.

Referring more particularly to FIG. 1, as the individual walks in the apparatuses 10, a first step causes the front mercury switch 140 to be deviated from horizontal to and beyond the predetermined attitude causing the switch closure 243 to close thereby supplying electrical energy to the buzzer 162 causing it to sound. During the same step, the rear mercury switch 150 may or may not close depending upon the attitude of the mercury switch and the sensitivity thereof previously described. As the apparatus 10 is placed back on the surface of support, both front and rear mercury switches open, having reached horizontal attitudes, thereby terminating the flow of electrical energy to the buzzer 162 and terminating its operation. As forward motion is continued in the normal walking motion, the rear portion 41 of the shoe 20 is elevated from the surface of support to move the rear mercury switch 150 to and beyond the predetermined attitude from horizontal. Thus, electrical energy is again supplied to the buzzer 162 from the source of electrical energy 161 to cause it to sound. As motion is continued, the front mercury switch 140 will ultimately be moved again to and beyond the predetermined attitude causing the switch to close. However, once the apparatus 10 is again placed flat on the surface of support, the front and rear mercury switches will again open terminating the flow of electrical energy to the buzzer 162 and terminating its operation.

It will be visualized that a person wearing two such apparatuses 10 will operate the buzzers 162 thereof in different sequence indicating the longitudinal tilt fore and aft of each foot during the walking process. Thus, a record can be made of the fore and aft longitudinal tilt of the feet of the individual during, as nearly as the individual is capable, a normal gait. This can be employed by the person conducting the test in developing a program of rehabilitation for the individual. Alternatively, or in addition, the sounding of the buzzers 162 can be employed by the person as a tool in achieving the optimum sequence of sound and thereby fore and aft longitudinal tilt with or without the presence of the person conducting the test. Thus, the apparatuses 10 can be employed by the individual at home, or away from the facility, to practice on improving the physical capability which is the subject of the test and requires rehabilitation.

In the case of the apparatuses 210, the orientation of the front and rear mercury switches 340 and 350, respectively, along axes transverse to the longitudinal axis of the support block 305, means that these mercury switches are not closed by fore and aft longitudinal tilt during the walking motion. These mercury switches are closed only by lateral tilt in either direction. As in the case of the apparatuses 10, the interior and anterior filling material 330 and 331 of the apparatuses 210 provides moderate lateral support so that a normal walking motion is possible. However, the moderate flexibility of the filling material and of the base plate 321 is such that limited tilting is possible thereby making detection of the lateral tilt possible.

The individual wearing both of the apparatuses 210 walks in a normal walking motion, within his or her physical capability, along a preselected course as directed by the person conducting the test. Each apparatus 210 independently records the lateral tilt of each foot of the individual during this walking motion by sounding the buzzer. Thus, as may be visualized upon reference to FIG. 5, if the person walking tilts outwardly with his or her left foot during the walking motion, the front and rear mercury switches 340 and 350 on the right as viewed in FIG. 5 will be elevated to and beyond the predetermined attitude beyond horizontal causing those switches to close. As a consequence, electrical energy is supplied to the buzzer 362 from the source of electrical energy 361 causing the buzzer to sound. Conversely, if the lateral tilt of the left foot is inwardly, the front and rear mercury switches 340 and 350 on the left as viewed in FIG. 5 will be elevated to and beyond the predetermined attitude causing those switches to close and thereby similarly supplying electrical energy from the source to the buzzer 362. In either case, the buzzer will sound for the period of time that the apparatus 210 is not disposed in a substantially horizontal attitude.

If, as with apparatuses 10, it is visualized that the individual walking has this change in attitude recorded for both feet at the same time, it will be seen that a record for both feet is, in effect, created. Thus, the person conducting the test develops a record from which to design a program of rehabilitation adapted to the specific needs of the individual being tested. Similarly, and as with apparatuses 10, the apparatuses 210 can be employed at home by the individual to practice achieving the desired walking motion without the lateral tilt since the buzzer sounds at any time such tilt takes place.

In accordance with the method of the present invention, the person conducting the test, in the case of both apparatuses 10 and 210, registers the information gathered during the test for the individual, evaluates the information and develops a program of rehabilitation designed to the specific needs and physical capability of that test individual. The person conducting the test then personally directs the individual, or has others do so, in the program of rehabilitation designed from the test results.

The apparatuses 10 and 210 are representative of a multitude of embodiments of the present invention as previously noted. Thus, for example, the support block 105 in apparatus 10 can be made wider or narrower as viewed in FIG. 1 or moved forwardly or rearwardly in specific embodiments of the measuring assembly 90. Thus, a person conducting such tests can have a multitude of different measuring assemblies 90 having different physical attributes as previously set forth for purposes of individually testing the physical capabilities of test subjects. The measuring assemblies 90 can be removed from the apparatus 10 simply by removing the bolts 98 and replacing the measuring assembly with one having the different internal structure. Other variables in the measuring assembly can include having the base plate 121 disposed at a different attitude than parallel to the shoe 20. Similarly, and as previously noted, the support block itself can be constructed of a moderately flexible material, such as crepe rubber, or synthetic rubber, depending entirely on the test information desired to be acquired by the person conducting the test.

These variations can also be employed in the case of the measuring assemblies 290 of the apparatus 210.

Still further, the electrical sensing systems 160 and 360 of the apparatuses 10 and 210 can be varied as desired by the person conducting the test. Thus, the buzzers 162 and 362 can be replaced by signal lights. The source of electrical energy can be a battery or an electrical cable connected to a wall outlet. In the place of the buzzers 162 and 362, or in addition thereto, the electrical sensing systems 160 and 360 can be connected to any suitable recording device operable to record as to time and/or space when the mercury switches are closed and when they were opened so as to provide a precise physical record of tilt either longitudinally or laterally during the tests using the apparatuses 10 and 210.

Therefore, the method and apparatus for sensing and evaluating foot borne motion of the present invention are operable effectively to isolate and measure the physical capabilities required for such foot borne motion; have a wide application to individuals having a multitude of different physical capabilities; are similarly adapted to sensing and evaluating a variety of foot borne motions including walking and running; and can conveniently and inexpensively be employed by doctors, physical therapists and others in the testing and/or treatment of individuals requiring such rehabilitation.

Although the invention has been herein shown and described in what is conceived to be the most practical and preferred embodiments, it is recognized that departures may be made therefrom within the scope of the invention which is not to be limited to the illustrative details disclosed.

Having described my invention, what I claim as new and desire to secure by Letters Patent is:

1. A method for evaluating foot borne motion in an individual comprising:
   applying footwear to at least one foot of said individual having means for registering predetermined movement of said foot relative to an axis of reference during foot borne motion;
   causing said individual to engage in said foot borne motion; and
   detecting said predetermined movement of the foot relative to said axis of reference during said foot borne motion.

2. An apparatus for evaluating foot borne motion in an individual comprising a support member, footwear mounting said support member thereon and adapted to attach said support member to a foot of said individual, means borne by the apparatus for detecting predetermined movement of the foot during said foot borne motion, and wherein said footwear has a mounting assembly on a lower portion thereof operable releasably to mount said support member on said lower portion of the footwear so as to permit support members of different operational capabilities to be mounted thereon.

3. The apparatus of claim 2 wherein said detecting means includes a sensor mounted on the support member.

4. The apparatus of claim 3 wherein said support member has a lower surface deployed for contact with a surface of support during said foot borne motion, said support member is oriented along a longitudinal axis and said sensor is operable to detect said predetermined movement relative to said longitudinal axis.

5. The apparatus of claim 4 wherein the support member has a forward portion and a rearward portion, two sensors are mounted in the forward portion on opposite sides of said longitudinal axis and two sensors are mounted in the rearward portion on opposite sides of said longitudinal axis.

6. The apparatus of claim 4 wherein said sensor is a mercury switch operable to close when said mercury switch is moved from a substantially horizontal attitude.

7. The apparatus of claim 4 wherein said support member has means for destabilizing said foot borne motion.

8. The apparatus of claim 7 wherein said destabilizing means includes a portion of said support member operable substantially to create a position about which said foot moves during said foot borne motion and a portion of the support member which flexes to accommodate the movement of the foot about said position.

9. The apparatus of claim 8 wherein said sensor is a normally open switch and the apparatus includes an electrical system having a source of electrical energy, a signalling mechanism and an electrical circuit operably interconnecting said switch, signalling mechanism and source of electrical energy and being operable during said foot borne motion to supply electrical energy from said source of electrical energy to the signalling mechanism upon closure of said normally open switch to activate the signalling mechanism to signal when said predetermined movement has occurred during said foot borne motion.

10. The apparatus of claim 9 wherein said switch is a mercury switch operable to remain open when disposed in a substantially horizontal attitude and to close upon reaching a second predetermined attitude deviated from said substantially horizontal attitude.

11. The apparatus of claim 9 wherein said signalling mechanism is a sound generating mechanism operable to indicate to said individual during said foot borne motion when said second predetermined attitude has been reached.

12. An apparatus for evaluating foot borne motion in an individual comprising a support member having a lower surface deployed for contact with a surface of support during said foot borne motion, oriented along a longitudinal axis and having means for destabilizing said foot borne motion; footwear for attaching said support member to a foot of said individual and having a mounting assembly on a lower portion thereof operable releasably to mount said support member on said lower portion of the footwear so as to permit support members having different destabilizing means to be mounted thereon; and a sensor mounted on the support member operable to detect predetermined movement relative to said longitudinal axis during said foot borne motion and wherein said destabilizing means includes a portion of said support member operable substantially to create a position about which said foot moves during said foot borne motion and a portion of the support member which flexes to accommodate the movement of the foot about said position.

13. A method for evaluating foot borne motion in an individual comprising:
applying footwear to a foot of said individual having a support member extending downwardly therefrom for engagement with a surface of support during foot borne motion and extending substantially along a predetermined axis and at least one sensor mounted on the footwear in predetermined relation to said axis operable to detect predetermined movement of the foot during said foot borne motion;
causing said individual to engage in said foot borne motion; and
registering said predetermined movement detected by the sensor during said foot borne motion.

14. The method of claim 13 wherein said sensor is operable to detect tilt laterally of said support member during said foot borne motion.

15. The method of claim 14 wherein said tilt laterally of said support member is registered during each step of said foot borne motion.

16. The method of claim 15 including the step of:
measuring the acceleration and deceleration in said tilt laterally of said support member during said foot borne motion.

17. The method of claim 13 wherein said footwear is applied to both feet of said individual during said applying, causing and registering steps and said registering is individually performed as to said feet.

18. The method of claim 17 wherein said foot borne motion is walking, said predetermined movement is lateral tilt and the method includes the step of:
evaluating the results registered in said registering step to determine the physical capability of said individual.

19. The method of claim 18 including the step of:
rehabilitating the physical capability of said individual.

* * * * *

UNITED STATES PATENT AND TRADEMARK OFFICE
CERTIFICATE OF CORRECTION

PATENT NO.   :   5,361,778
DATED        :   November 8, 1994
INVENTOR(S)  :   RONALD H. SEITZ It is certified that error appears in the above-identified patent and that said Letters Patent is hereby corrected as shown below:

```
Column 3, line 58, delete "tipper" and substitute
     ---upper---.

Column 4, line 29, delete "tipper" and substitute
     ---upper---.

Column 4, line 54, delete "tipper" and substitute
     ---upper---.

Column 5, line 3, delete "tipper" and substitute
     ---upper---.

Column 6, line 55, delete "tipper" and substitute
     ---upper---.

Column 10, line 9, delete "tie" and substitute
     ---be---.

Column 11, line 8, delete ":" before the word "for".
```

Signed and Sealed this

Third Day of January, 1995

Attest:

BRUCE LEHMAN

*Attesting Officer*    *Commissioner of Patents and Trademarks*